United States Patent

Jimenez Ramos

Patent Number: 5,672,156
Date of Patent: Sep. 30, 1997

[54] DEVICE TO AVOID TWISTS IN ANKLES

[76] Inventor: Antonio Jose Jimenez Ramos, Ronda de Sobradiel, No. 29 C-Purque del conde de Orgaz, Madrid, Spain

[21] Appl. No.: 494,849

[22] Filed: Jun. 26, 1995

[30] Foreign Application Priority Data

Jun. 24, 1994 [ES] Spain ................ 9401387

[51] Int. Cl.$^6$ .................. A61F 5/00; A43B 7/20
[52] U.S. Cl. .................. 602/27; 36/89; 602/23
[58] Field of Search .................. 602/23, 27, 28, 602/29; 36/88, 89, 115, 140

[56] References Cited

U.S. PATENT DOCUMENTS

| | | | |
|---|---|---|---|
| 604,044 | 5/1898 | Hamel et al. | 602/27 |
| 1,638,285 | 8/1927 | Brooks | 602/27 |
| 2,450,862 | 10/1948 | Wilkinson | 602/27 |
| 2,632,440 | 3/1953 | Hauser et al. | 602/23 X |
| 4,719,926 | 1/1988 | Nelson | 602/27 |
| 4,809,686 | 3/1989 | Crane | 602/27 |
| 4,865,023 | 9/1989 | Craythorne et al. | 602/27 |
| 4,922,630 | 5/1990 | Robinson | 602/27 X |
| 4,936,295 | 6/1990 | Crane | 602/29 |

Primary Examiner—Linda C. Dvorak
Attorney, Agent, or Firm—Marks & Murase

[57] ABSTRACT

An independent, removable device which is capable of being attached to the leg above the ankle and to the external side of the footwear in a variety of ways prevents ankle injuries. The device comprises a strap (1 in every figure) which embraces the leg of the wearer, just over and around the ankle. At the ends of the strap there is a suitable system to close the strap. The upper end of a rigid or semirigid sheet (2 in every figure) is pivotally connected to the strap (1). The lower end of the sheet is inserted in a little box (4 in every figure), which is fitted to the side of the shoe. The connection of the sheet to the shoe also might be done through a screw which would be screwed on the shoe sole (8 in FIG.3).

5 Claims, 5 Drawing Sheets ial injury.
DEVICE TO AVOID TWISTS IN ANKLES

FIELD OF THE INVENTION

The present invention relates the to field of preventing ankle injuries. More specifically, the present invention relates to footwear and an associated device for preventing ankle injuries.

BACKGROUND OF THE INVENTION

The present invention, as stated, relates to a removable device to avoid twists in ankles.

The twist of the ankle is something that occurs at any age and in many forms. It is not necessary to be practicing a sport to suffer a sprain. Even walking in the city, one can twist the ankle with major or minor damage and consequences. Sometimes the injury entails no more than a slight pain but, in other cases, a support bandage must be worn until the injury heals.

Clearly, there is a major possibility of ankle injuries when playing sports on an irregular surface, or in those games that require frequent jumps (such as basketball). Ankle injuries are also common in those sports that subject the ankles muscles to sudden and intense strain (such as parachuting) or, sports that combine turns and supports in terrain of varied hardness.

Sprains and the risk of sprains occur principally when we require more of our body than it is prepared to give. Those who have suffered an ankle injury are often hesitant to stop training and therefore have a repetition of the injury because they did not allow time for total recuperation of the muscles of the affected zone. Obviously, the second injury will likely have consequences that are quite serious.

Many people, given their physiology, have a certain propensity to sustain ankle injuries and are therefore at increased risk when participating in sports that require the effort of legs and the consequent fatigue of such muscular groups. Likewise, it is frequently true that people who have suffered some sprain, remain weakened from the incident and have a certain tendency to suffer injuries that affect the zone formerly hurt.

At the present time, in the professional and amateur sports world, there are numerous ankle twists and even sprains of varying severity experienced by people that participate in sports that require intense physical effort using the ankles, such as soccer, basketball and others.

To avoid these injuries, people used different kinds of preventive devices, like elastic socks and support bandages applied in the zone of the ankles.

In spite of these different types of preventive devices, the result is generally inefficient, especially when a sudden physical effort or range of motion of the ankles is excessive. Then an ankle twist or sprain occurs.

Thus, a need exists for a device which can prevent ankle injuries or protect an ankle from further injury during training following an ankle injury.

SUMMARY OF THE INVENTION:

With the end of preventing and to avoid the twists or sprains of the ankle, the invention proposes a novel and advantageous removable device that fits easily and rapidly to the footwear. In the ease of an ankle being twisted, this device avoids the excessive extension of the muscles and ligaments of the ankle, avoiding consequently the injury.

In the case of a person in a recuperation period from a sprain, the present invention allows the person to continue habitual training with confidence of being protected from a similar setback caused by the original injury.

In order to give a solution to the preceding problems mentioned, the invention proposes an advantageous removable device to avoid twists in ankles.

This device involves a strap of any material that embraces around the superior part of the ankle; this strap is pivotally joined to a rigid or semirigid sheet, which has an end inserted in a little box which is fitted to the side of the sport shoe. The little box could be located in different parts of the exterior zone of the footwear such as the side of the sole or in the proper cut of the footwear. Preferentially, the box might be placed in the side of the upper sole given that this part has a major consistency And solidity. The connection of the sheet to the sport shoe also can be done by other different forms.

The vertical sheet presents a certain rigidity and thus a controlled flexibility; this sheet does not allow the bending when an excessive movement is committed, avoiding the twist or the ankle injury.

Thus, the removable device of the present invention has great effectiveness to avoid injuries of the ankles. At the same time, it is not uncomfortable for the wearer given that the strap is wrapped around the top of the ankle and the sheet does not touch the ankle bone. Moreover, the total weight of the device is insignificant.

In order to facilitate comprehension of the present invention, a series of figures is included which illustrate some embodiments and the object of the invention.

DETAILED DESCRIPTION OF THE INVENTION AND ITS COMPONENTS

Figure 2:
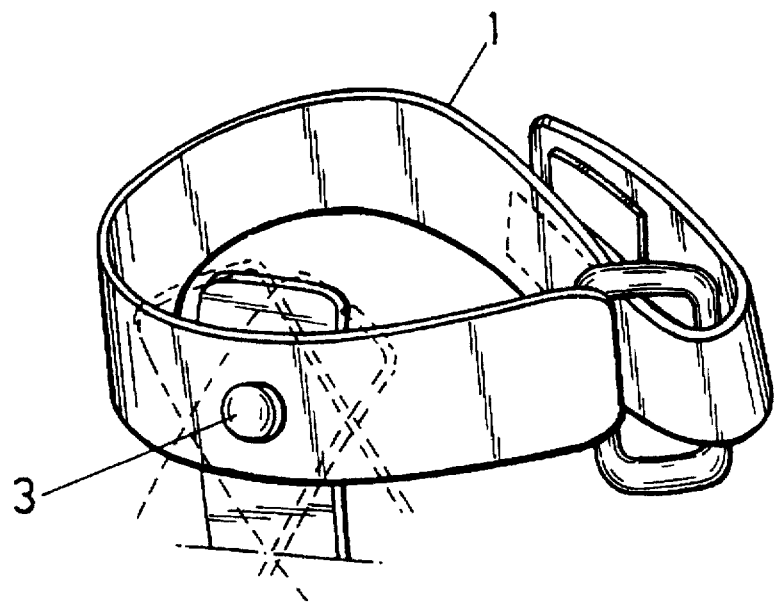
FIG. 2 is a perspective view of the upper part of the device, showing the same by a strap which connects pivotally to a rigid or semirigid sheet.

In accordance with the numbering adopted in the figures, the removable device to avoid ankle twists has a strap (1 in every figure) of natural material, like leather, or made with synthetic material, like nylon, polyester or others. This strap (1) surrounds the superior part to the ankle embracing the lower zone of the leg. At the ends of the mentioned strap there is an appropriate system of hooks or closing, such as fabric hook and eye fasteners (VELCRO®), plastic buckles and others for securing the strap around the leg above the ankle. The fastener for the strap might be achieved with the combination of two or more systems among those mentioned; for example, the buckles and the fabric hook and eye fasteners (FIG. 2).

Figure 1:
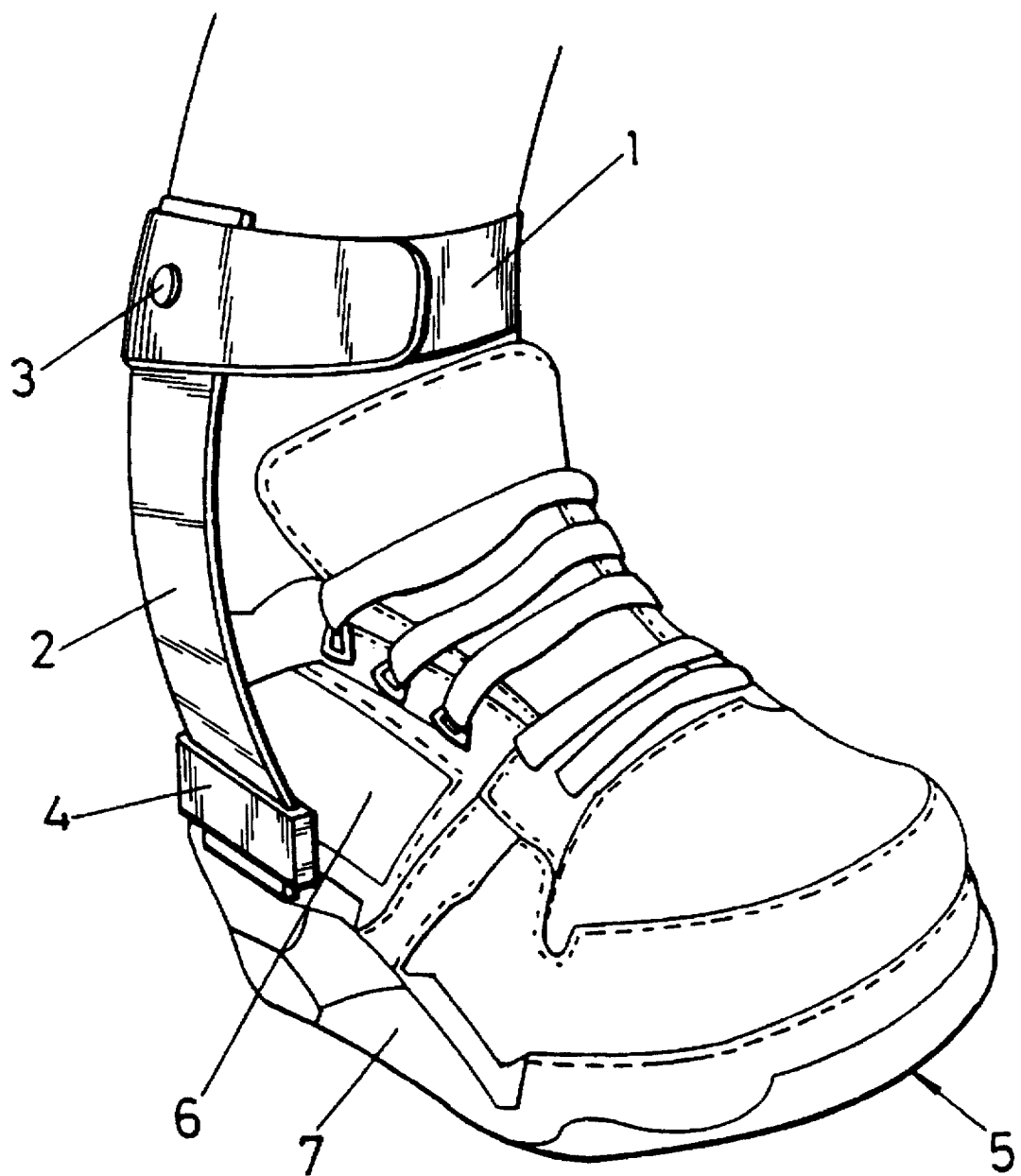
FIG. 1 is a perspective view of the removable device to avoid ankles twists according to the invention. The device is superiorly embraced to the ankle through a strap, which is joined to a rigid or semirigid sheet with a lower end inserted in a little box which is fitted to the external side of the footwear.
Figure 5:
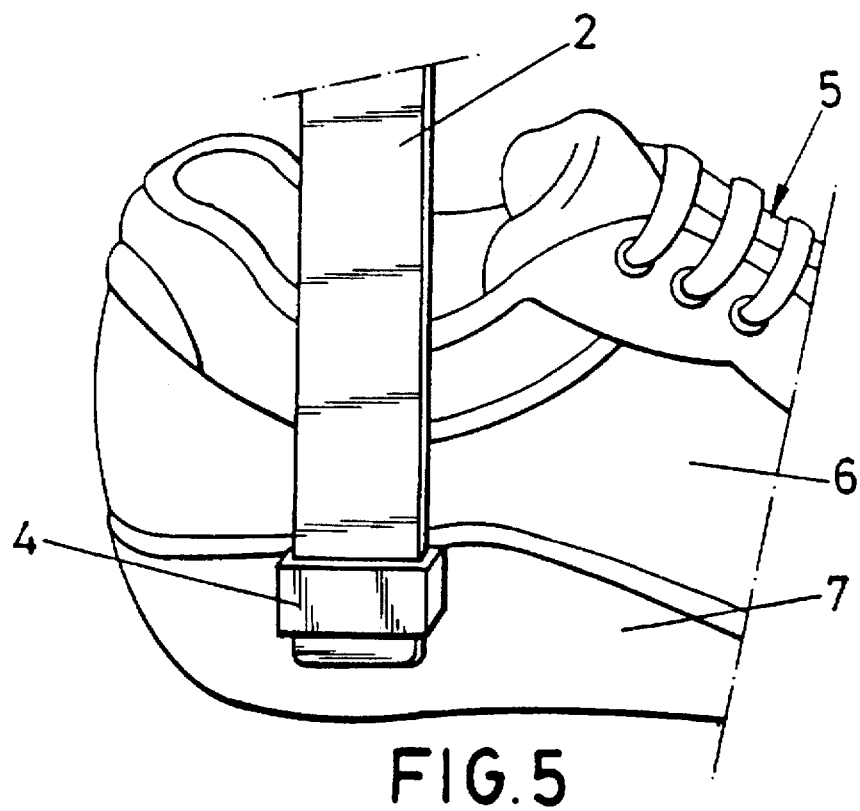
FIG. 5 is a view wherein is shown another connection of the sheet to the footwear.
Figure 6:
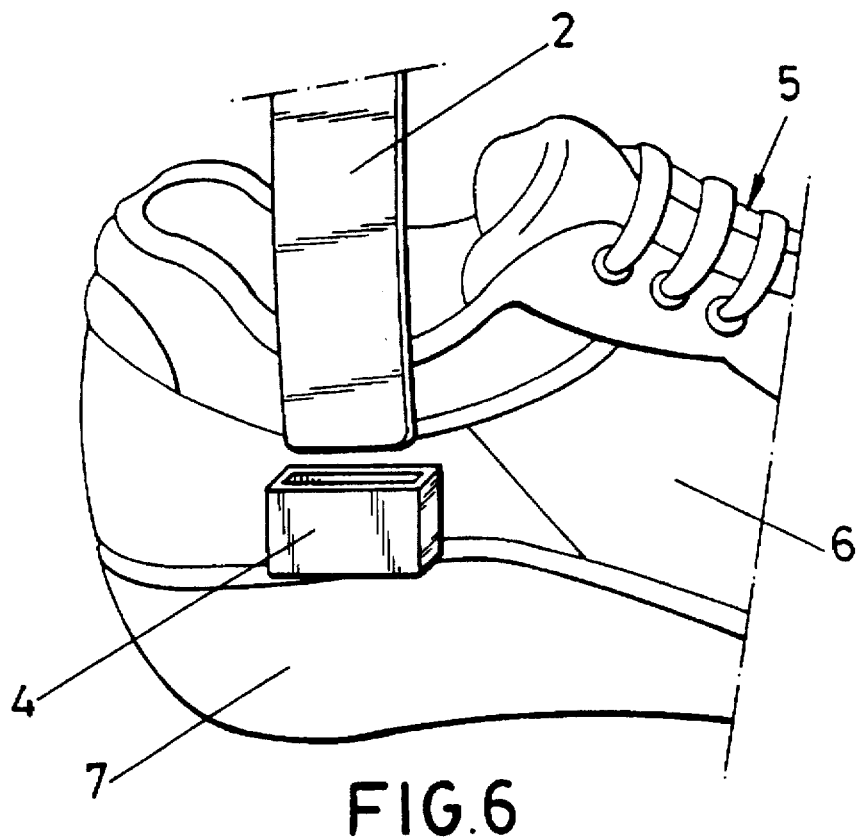
FIG. 6 is a view wherein is shown the little box fitted to the footwear.

The strap (1 in FIG. 1) is pivotally joined to a rigid or semirigid sheet (2 in FIG. 2) with a screw or a rivet (3 in FIG. 1) which allows the sheet a reasonable movement. The lower end of the sheet is inserted in a little box or something similar (4 in FIG. 1) fixed at the external part of the corresponding footwear. The mentioned little box (4 in FIG. 1) might be fixed in the side of the footwear (6 in FIG. 1) or in the side of the sole (4 in FIG. 5).

Figure 3:
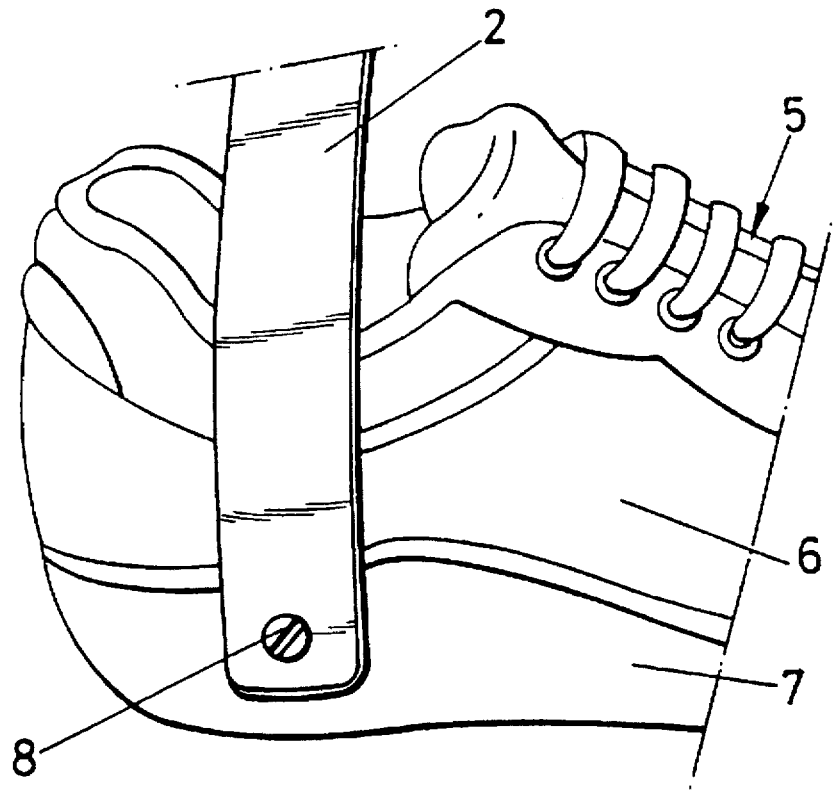
FIG. 3 is a perspective view wherein a very particular connection of the sheet to the external side of the sole by a screw is shown.
Figure 4:
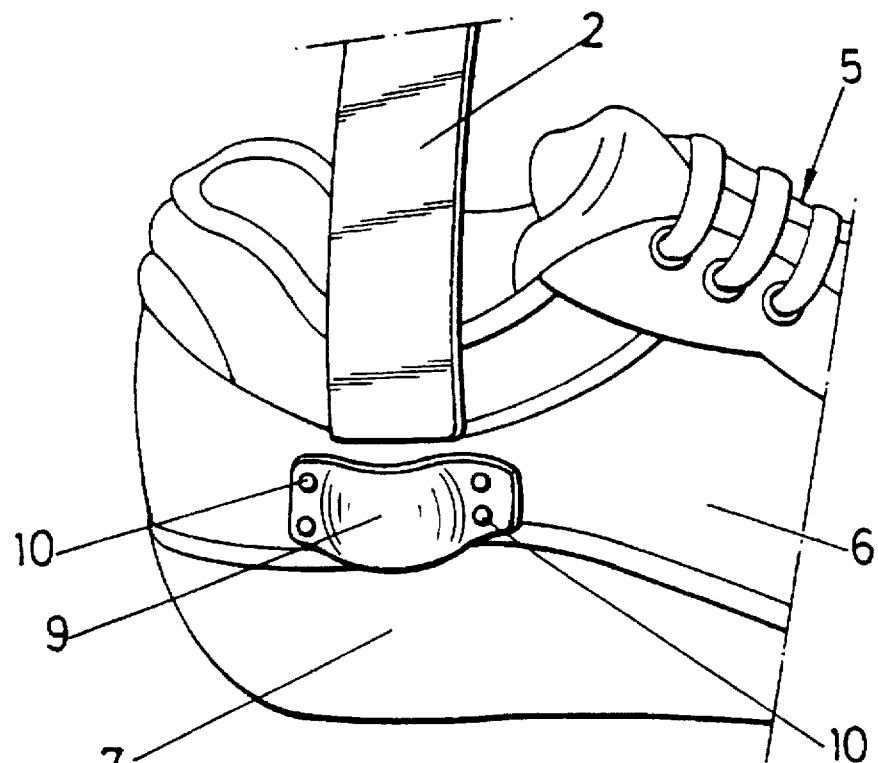
FIG. 4 is a view wherein is shown a different connection of the sheet to the footwear.

In the alternative, the connection between the vertical sheet (2 in every figures) and the footwear might be done with a screw (8 in FIG. 3) screwed to the sole of the footwear. Another system would consist in a reinforcement (9 in FIG. 4) fixed to the side of the footwear by rivets (10 in FIG. 4).

Figure 7:
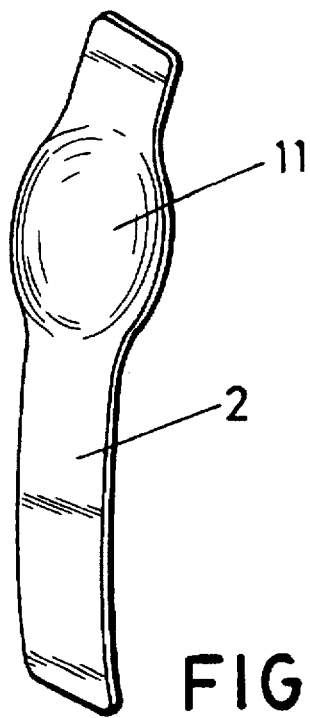
FIG. 7 is a perspective view of a sheet which has been shaped corresponding with the external pattern of the ankle bone.

Although the sheet generally will be rectangular and lengthened, it also is susceptible to be shaped (11 in FIG. 7) or bent in some parts with the end to facilitate its function.

Figure 8:
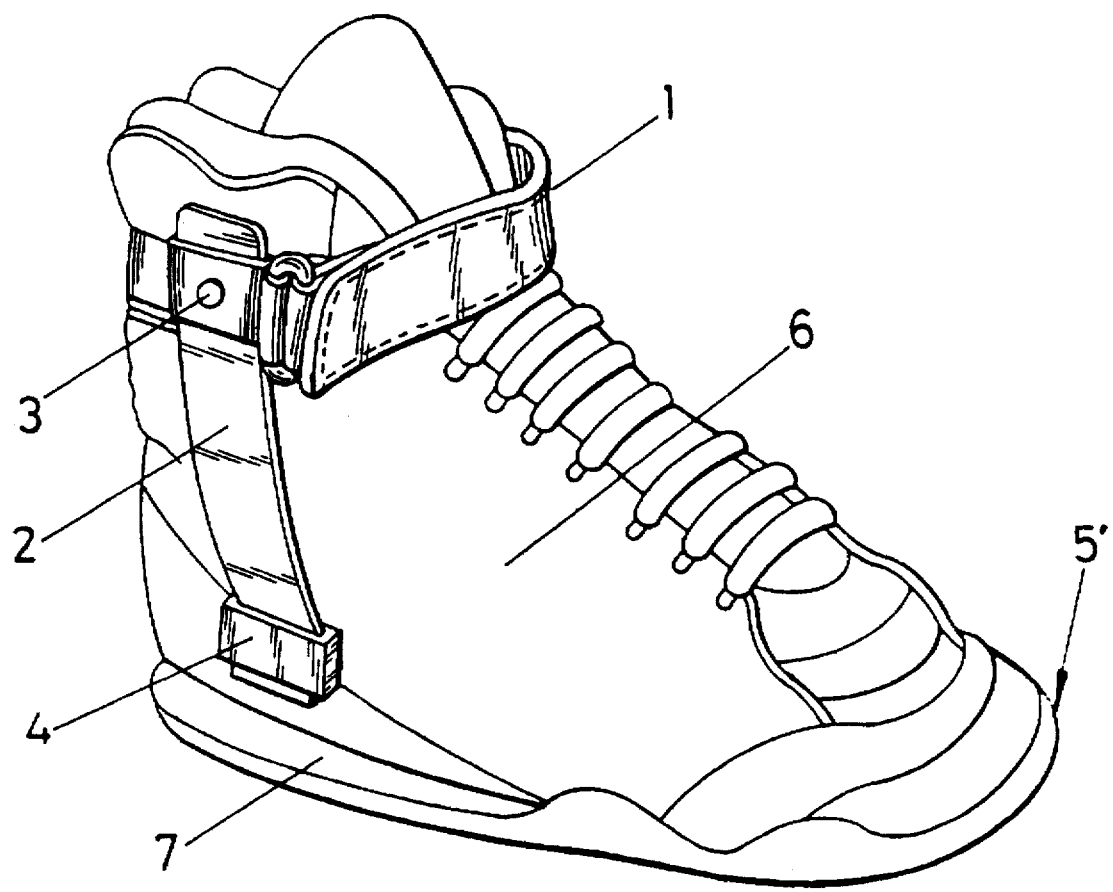
FIG. 8 is a perspective view of a sport boot that incorporates the device of the invention.

The system applied in sport boots (FIG. 8) is basically the same as that applied in the normal footwear.

The little box (4 in every figure) is made of any natural leather or any synthetic material like polyester, polypropylene, nylon, acetyl or any thermoplastic. It is fixed to the external side of the footwear or even to the sole. Furthermore and not less important is the feature of this little box to allow the easy entrance and removal of the sheet in itself.

The sheet (2 in every figure) can also be made of any adequate synthetic material like polyester, polypropylene, nylon, acetyl or any thermoplastic. This sheet also might be made of any light metal or alloy.

The measure of this sheet allows a certain mobility in the interior of the mentioned little box fixed to the footwear. Also the sheet might have a component to reflect rays of light.

People using this device will avoid advantageously the twists or ankle sprains given that, when an excessive effort or range of motion is produced in the zone of the ankles and directed toward outside, it is neutralized advantageously by the sheet (2) which does not allow the excessive stretching of the ankles ligament, avoiding the painful injury.

As it has been emphasized before, a fundamental feature of this device is its;ability to be removable, being susceptible to be fitted to the footwear with great facility.

I claim:

1. A device for preventing twisted ankles comprising:

a shoe having a sole and an upper;

strap means, separate from said shoe, for encircling a leg above an ankle;

a substantially rigid sheet, an end of which is pivotally connected to said strap means; and a box attached to said shoe which receives said rigid sheet therein.

2. A device as claimed in claim 1, wherein an end of said rigid sheet is inserted into said box, but is not attached thereto.

3. A device as claimed in claim 2, wherein said box has no bottom and allows said sheet to pass completely through said box.

4. A device as claimed in claim 2, wherein said rigid sheet may be instantly removed from said box.

5. A device as claimed in claim 1, wherein said rigid sheet is shaped to accommodate the contours of an anklebone.

* * * * *